Figure 1:
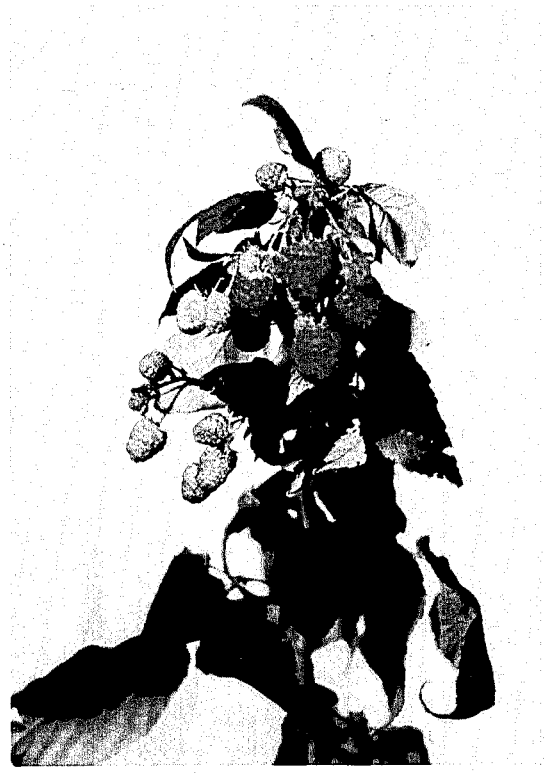

United States Patent [19]

Sanford et al.

[11] Patent Number: Plant 7,067

[45] Date of Patent: Dec. 5, 1989

[54] RED RASPBERRY 'WATSON'

[75] Inventors: John C. Sanford; Jack E. Reich, both of Geneva, N.Y.

[73] Assignee: Cornell Research Foundation, Inc., Ithaca, N.Y.

[21] Appl. No.: 264,551

[22] Filed: Oct. 28, 1988

[51] Int. Cl.[4] ..... A01H 5/00

[52] U.S. Cl. ..... Plt./46

[58] Field of Search ..... Plt./46

*Primary Examiner*—Robert E. Bagwill

*Attorney, Agent, or Firm*—Jones, Tullar & Cooper

[57] ABSTRACT

A red raspberry plant, 'Watson' (also tested as NY 114), which produces primocane fruit, which are very large and abundant.

3 Drawing Sheets

SUMMARY

This invention is a new and distinct variety of fall-bearing red raspberry, known as 'Watson', (also tested as NY 114) which is exceptional for its large, firm fruit and high yield potential.

ORIGIN

This new cultivar was developed by the small fruits breeding program of the Department of Horticultural Sciences, Cornell University, NYSAES, Geneva, N.Y. The cross was 'Heritage'×'Titan', and was made in 1980. The selection was made in 1983, and has been tested at Geneva and by cooperative testers from 1984–1988 as NY 114.

DESCRIPTION

'Watson' suckers aggressively on fertile soil, and is vigorous. Canes are green, with spines distributed quite uniformly and quite sparsely along primocanes and on petioles. Spines have stout bases and sharp tips (painful to the touch). Spines are green except near the tips, where they are red. Spines are reflexed downward (basally) slightly. Petioles are attached to the stem at a distinctly narrower (more upright) angle, compared to the 'Heritage', and especially the 'Titan' parent.

'Watson' stipules are smaller, especially on the top half of the cane, than either parent, and are entirely green in color. Leaves are light green, especially near the primocane tips, where they are yellowish green. Near Primocane tips, leaflets are distinctly narrow and long. The upper surface of the leaves are hairy. The summer ("fruiting cane") crop of fruit is small and unimpressive. The fall crop of fruit is large in size. The fruit are consistently 40–50% larger than 'Heritage', making 'Watson' larger than any other commercial fall-bearing raspberry commonly available at present. In 1988, in Geneva, N.Y., at the beginning of the fall season, average fruit weight was 2.5 g for 'Watson' and 1.6 g for 'Heritage'. In California average berry size is up to 4.2 g/berry. The fruit is conic in shape, with uniform drupelet size, and bright red color. Fruit hangs pendant on the primocanes. The fruit are very firm and separate easily from the large torus. 'Watson' flavor is comparable to 'Heritage'. The fruit are relatively dry in handling, and do not "bleed", making them superior for shipping. Yields are large and appear to be as good as 'Heritage'. Yields are as high as 4.5 tons/acre. Fruiting season is approximately the same as for 'Heritage', but can vary. In Geneva, N.Y., 'Watson', may be several days earlier or later than 'Heritage'. On sandy soils in Massachusetts, 'Watson' tends to be several days to 1 week earlier than 'Heritage'. In the Watsonville, Calif. area, 'Watson' tends to 'peak' 2–4 weeks later than 'Heritage', extending the fruiting season. 'Watson' is particularly susceptible to Phytophthora root rot and Botrytis fruit rot, but is resistant to the yellow rust disease, and is less susceptible to powdery mildew than 'Heritage'. To avoid Phytophthora problems, 'Heritage' should be grown on light, well-drained soils.

'Watson' can be distinguished from its parents in the following ways. While 'Titan' is summer-bearing only, with wide petiole angle and no hairs on the upper leaf surface — 'Watson' has a poor summer crop but a strong fall crop, with upright leaf angle and upper leaf hairs. 'Heritage' differs from 'Watson' in having smaller, non-pendant fruit, more abundant, longer, thinner spines, a reddish hue to its youngest leaves, and enlarged nodes — with the base of the petiole being more swollen. 'Watson' is less erect than the 'Heritage', and should be trellised.

'Watson' Colors

According to The Royal Horticultural Society (R.H.S.) colour Chart, 'Watson' colors can be characterized as shown below. It must be kept in mind that coloration in plants is highly dependent upon environmental conditions such as light, temperature, stress, etc. Therefore, these colors can only be considered approximations:

1. Stem color (shaded): yellow green 145b–145c.
2. Stem color (full sun): grayed purple 184a.
3. Leaf color (mature): green 137a–137b.
4. Leaf color (primocane tips): yellow green 144a.
5. Fruit color: red 53a.

DESCRIPTION OF PHOTOGRAPHS

FIG. 1. Fruiting terminal of 'Watson' primocane. Note large fruit size, causing fruit to be 'pendant' (hang down) like the 'Titan' parent, unlike other fall-bearing varieties.

Figure 2:
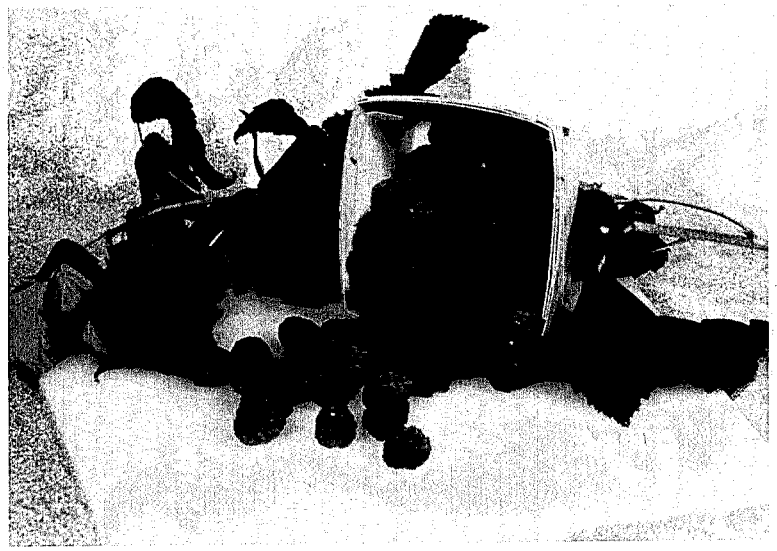

FIG. 2. Fruit of 'Watson' "spilling" from a pint basket. Note size, bright color and attractive appearance.

Figure 3:
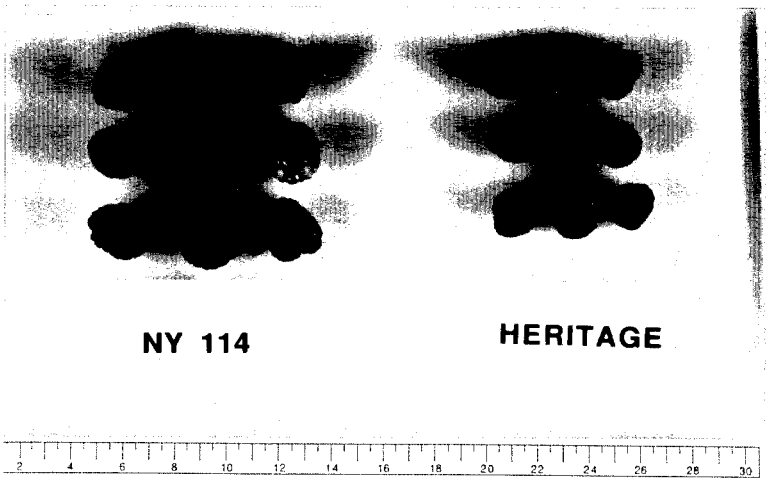

FIG. 3. Fruit of 'Watson' contrasted to 'Heritage' fruit. Note that 'Watson' fruit are clearly larger in size, with larger drupelets than 'Heritage' (scale on bottom of figure shows centimeters).

Figure 4:
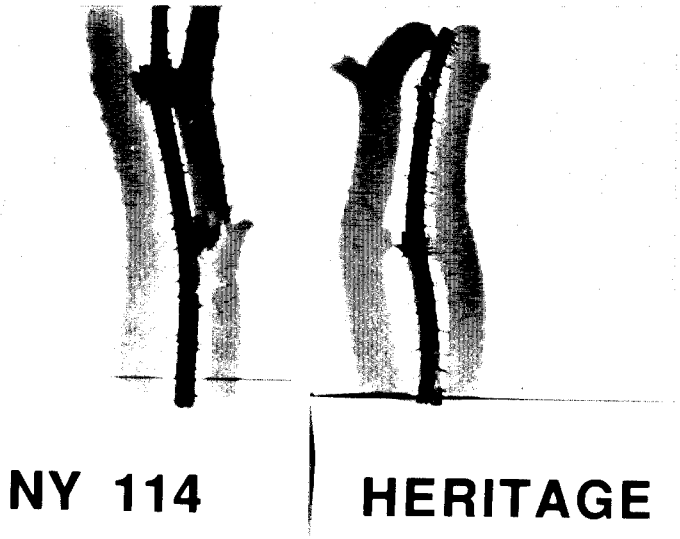

FIG. 4. Spines of 'Watson' contrasted to 'Heritage'. Note that 'Watson' spines are more sparse, tend to hook downward more, are shorter in length and thicker at the base (more 'stout') than spines of 'Heritage'.

Figure 5A:
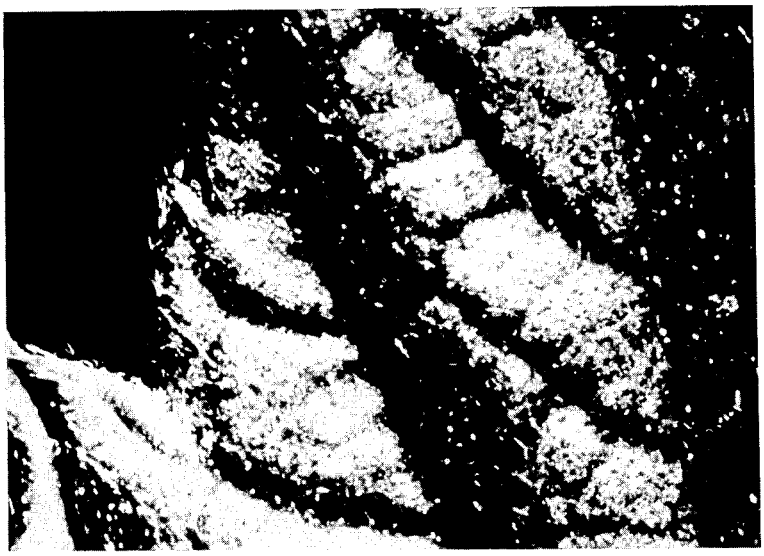

FIG. 5*a*. Upper leaf surface of 'Watson' (magnified) showing abundant surface hairs.

Figure 5B:
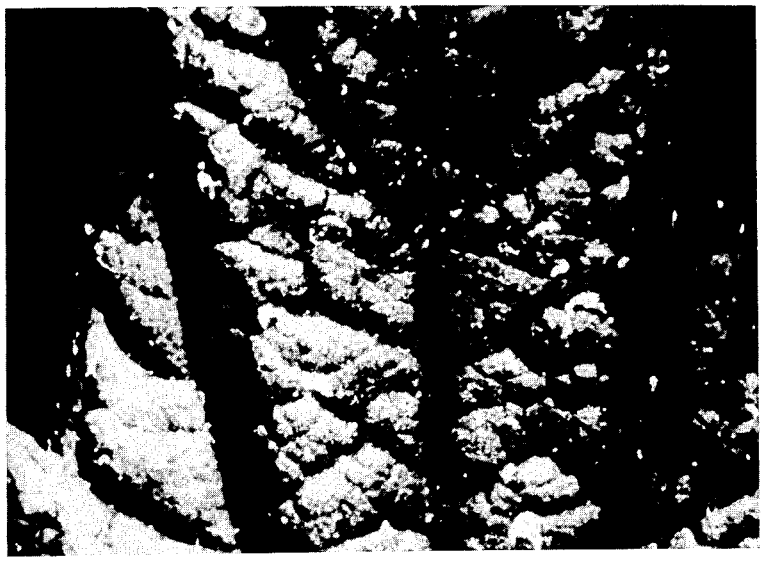

FIG. 5*b*. Upper leaf surface of 'Titan' (same magnitification) showing near absence of surface hairs.

MERITS

'Watson' has distinctly larger fruit than the other fall-bearing raspberries commonly available in North America. This greatly aids in harvest, and reduces labor expenses. 'Watson' has proven especially well adapted to the area near Watsonville, Calif. where raspberries are grown commercially for fresh fruit shipment. The fruit are very firm and dry, making them well suited for long-distance shipment. The plants appear to be resistant to the yellow rust disease, a serious problem in that region. In these respects 'Watson' is superior to 'Heritage' as a commercial fall-bearing raspberry.

We claim:

1. The new and distinct variety of red raspberry herein described, illustrated, and identified by the characters enumerated above.

* * * * *